United States Patent
Nakajima et al.

(10) Patent No.: US 7,122,024 B2
(45) Date of Patent: Oct. 17, 2006

(54) OPEN-TYPE DISPOSABLE WEARING ARTICLE HAVING BIFURCATED STRETCHABLE ZONES

(76) Inventors: Kaiyo Nakajima, c/o Technical Center, Uni-Charm Corporation, 1531-7 Takasuka, Wadahama, Toyohama-cho, Mitoyo-gun, Kagawa-ken (JP); Yoshitaka Mishima, c/o Technical Center, Uni-Charm Corporation, 1531-7 Takasuka, Wadahama, Toyohama-cho, Mitoyo-gun, Kagawa-ken (JP); Tomoko Sugito, c/o Technical Center, Uni-Charm Corporation, 1531-7 Takasuka, Wadahama, Toyohama-cho, Mitoyo-gun, Kagawa-ken (JP)

( * ) Notice: Subject to any disclaimer, the term of this patent is extended or adjusted under 35 U.S.C. 154(b) by 470 days.

(21) Appl. No.: 10/603,008

(22) Filed: Jun. 24, 2003

(65) Prior Publication Data
US 2004/0006326 A1    Jan. 8, 2004

(30) Foreign Application Priority Data
Jun. 24, 2002    (JP)    .............................. 2002-183415

(51) Int. Cl.
*A61F 13/475*    (2006.01)
*A61F 13/62*    (2006.01)
*A61F 13/49*    (2006.01)
(52) U.S. Cl. ........................... 604/385.25; 604/385.24; 604/391; 604/386; 604/385.01
(58) Field of Classification Search ........... 604/385.01, 604/385.22, 391, 385.24–385.25
See application file for complete search history.

(56) References Cited

U.S. PATENT DOCUMENTS

| 3,000,381 | A |  | 9/1961 | Mulhole et al. |
| 3,882,871 | A |  | 5/1975 | Taniguchi et al. |
| 4,355,425 | A | * | 10/1982 | Jones et al. .................... 2/402 |
| 4,425,128 | A |  | 1/1984 | Motomura et al. |

(Continued)

FOREIGN PATENT DOCUMENTS

EP    1 201 212    5/2002

(Continued)

OTHER PUBLICATIONS

Ciullo, Peter and Norman Hewitt. The Rubber Formulary. Norwich: Noyes Publications, 1999, p. 60.*

(Continued)

*Primary Examiner*—Tatyana Zalukaeva
*Assistant Examiner*—Keshia Gibson
(74) *Attorney, Agent, or Firm*—Butzel Long

(57) ABSTRACT

An open-type disposable wearing article composed of a front waist region, a rear waist region and a crotch region. These regions are all elastically stretchable. The article includes first and second stretchable zones respectively bifurcated at a transverse middle of the crotch region so as to extend to lateral zones of the front and rear waist regions, respectively, and third stretchable zones defined by zones other than the first and second stretchable zones. The first and second stretchable zones exhibit a stretch stress higher than a stretch stress of the third stretchable zones. Loop members are provided to the second stretchable zone in the lateral zones of the rear waist region and hook members are provided to the first stretchable zone in the lateral zones of the front waist region.

8 Claims, 11 Drawing Sheets

U.S. PATENT DOCUMENTS

| | | | |
|---|---|---|---|
| 5,188,627 A * | 2/1993 | Igaue et al. | 604/385.27 |
| 5,411,498 A * | 5/1995 | Fahrenkrug et al. | 604/385.22 |
| 5,447,508 A | 9/1995 | Numano et al. | |
| 5,735,839 A | 4/1998 | Kawaguchi et al. | |
| 5,817,086 A * | 10/1998 | Kling | 604/385.19 |
| 5,855,573 A * | 1/1999 | Johansson | 604/385.17 |
| 6,120,485 A * | 9/2000 | Gustafsson et al. | 604/385.19 |
| 6,179,820 B1 | 1/2001 | Fernfors et al. | |
| 6,482,195 B1 * | 11/2002 | Kumasaka | 604/385.27 |
| 2001/0025165 A1 * | 9/2001 | Shimoe | 604/385.27 |
| 2004/0000268 A1 | 1/2004 | Wada et al. | |

FOREIGN PATENT DOCUMENTS

| | | |
|---|---|---|
| GB | 2 282 522 | 4/1995 |
| JP | 2001-8968 A | 1/2001 |
| WO | WO 97 43994 | 11/1997 |

OTHER PUBLICATIONS

Koshal, Dal. ed. Manufacturing Engineer's Reference Book. London: Butterworth-Heinemann, 1993, p. 1/75.*

* cited by examiner

OPEN-TYPE DISPOSABLE WEARING ARTICLE HAVING BIFURCATED STRETCHABLE ZONES

BACKGROUND OF THE INVENTION

The present invention relates to an open-type disposable wearing article.

Japanese Patent Application Publication No. 2001-8968A discloses an open-type disposable diaper comprising a first inner sheet which faces the wearer's body and is elastically stretchable in a transverse direction of the diaper, a first outer sheet which faces away from the wearer's body and is elastically stretchable in the transverse direction and an absorbent pad which is interposed between these first inner and outer sheets to configure a front waist region, a rear waist region and a crotch region extending between these waist regions wherein the crotch region is provided on its transversely opposite sides with second inner and outer sheets which are elastically stretchable not only in the transverse direction but also in a longitudinal direction of the diaper.

In this known diaper, the elastically stretchable first inner and outer sheets defining the front waist region, the rear waist regions and the crotch region facilitate the diaper to be put on the wearer's body because all of these regions are free from formation of gathers. To put this diaper on the wearer's body, tape fasteners attached to the opposite lateral zones of the rear waist region may be anchored on the opposite lateral zones of the front waist region so as to connect the front and rear waist regions with each other.

In the case of the diaper disclosed in the above-cited Publication, a contractile force of the first inner and outer sheets both being elastically stretchable in the transverse direction certainly serves to tighten the wearer's waist region in its circumferential direction.

However, the first inner and outer sheets are substantially non-stretchable in the longitudinal direction of the diaper and therefore do not intend to pull the crotch region of the diaper upward in the longitudinal direction. Consequently, it is impossible for this known-diaper to keep the crotch region of the diaper in close contact with the wearer's crotch region. Furthermore, longitudinally opposite end zones of the second inner and outer sheets are not connected together even after the diaper has been put on the wearer's body, so these second inner and outer sheets do not serve to tighten the wearer's legs in circumferential direction. In other words, it is impossible to utilize a contractile force of these second inner and outer sheets to tighten the wearer's legs.

SUMMARY OF THE INVENTION

It is an object of the present invention to provide an open-type disposable wearing article improved so that the crotch region can be kept in close contact with the wearer's crotch region and the inguinal region as well as the waist region of the wearer cap be properly tightened.

According to the present invention, there is an open-type disposable wearing article having a front waist region, a rear waist region and a crotch region extending between these waist regions, all being elastically stretchable, the front and rear waist regions being capable of connecting with each other along opposite lateral zones thereof.

The wearing article has a first stretchable zone bifurcated at a transverse middle of the crotch region so as to extend to the opposite lateral zones of the front waist region, a second stretchable zone bifurcated at the transverse middle of the crotch region so as to extend to the opposite lateral zones of the rear waist region and third stretchable zones defined by zones other than the first and second stretchable zones. A stretch stress of the first and second stretchable zones is higher than a stretch stress of the third stretchable zones; and first engageable means used to connect the front and rear waist regions with each other are provided in the second stretchable zone in the opposite lateral zones of the rear waist region and first receiving means releasably engaged with the first engageable means are provided in the first stretchable zone in the opposite lateral zones.

The present invention includes the following embodiments.

The first stretchable zone and the second stretchable zone are contiguous to each other at the transverse middle of the crotch region.

The first engageable means are first loop members attached to an inner surface of the rear waist region in the opposite lateral zones thereof and the first receiving means are first hook members attached to an outer surface of the front waist region in the opposite lateral zones thereof.

Second engageable means used to connect the front and rear waist regions are provided in the third stretchable zones lying in the opposite lateral zones of the rear waist region and second receiving means releasably engaged with the second engageable means are provided in the third stretchable zones lying in the opposite lateral zones of the front waist region.

The second engageable means are second hook members attached to the inner surface of the rear waist region in the opposite lateral zones thereof and the second receiving means are second loop members attached to the outer surface of the front waist region in the opposite lateral zones thereof.

The first stretchable zone lying in the opposite lateral zones of the front waist region and the second stretchable zone lying in the opposite lateral zones of the rear waist region are substantially connected with each other as the first engageable means are engaged with the first receiving means to put the wearing article on the wearer's body.

The wearing article is formed by a elastically stretchable fibrous nonwoven fabric having a basis weight thereof higher in the first and second stretchable zones than in the third stretchable zones.

The first and second stretchable zones each exhibit a stretch stress in a range of 0.25–30N when a width of the zones is 15 mm and the zones are stretched by 15% and a stretch stress in a range of 0.6–50N when a width of the zones is 15 mm and the zones are stretched by 40% and the third stretchable zone exhibits a stretch stress in a range of 0.17–20N when a width of the zone is 15 mm and the zone is stretched by 15% and a stretch stress in a range of 0.4–33N when a width of the zone is 15 mm and the zone is stretched by 40%.

The wearing article is used as a diaper cover adapted to be used together with an absorbent pad attached to a surface of the wearing article facing a wearer's body.

The open-type disposable wearing article according to this invention has advantageous effects that the first and second stretchable zones are elastically contractible in the longitudinal, i.e., the vertical direction, so the contractile force of these stretchable zones normally intend to pull the crotch region of the article upward. Such a feature ensures that the crotch region of the article is kept in close contact with the wearer's crotch region. The lateral zones of this article are defined by the third stretchable zones exhibiting a stretch stress lower than those of the first and second stretchable zones. This feature ensures that a wearer's free movement is never restrained by the first and second stretchable zones.

With the article in which the first and second stretchable zones are contiguous to each other in the transverse middle of the crotch region, the first and second stretchable zones cooperate to form an annular configuration extending from the wearer's inguinal region toward the wearer's waist region. This feature allows the contractile force of the first and second stretchable zones to be utilized to tighten the wearer's inguinal and waist regions.

With the article, the first engageable means must be engaged with the receiving means to connect the first stretchable zone to the second stretchable zone when the article is put on the wearer's body. In other words, it is impossible to bring the loop members attached to the lateral zones in the rear waist region in engagement with any members or zones other than the hook members when it is intentioned to put the article on the wearer's body. It is thus ensured that the lateral zones of the front waist region are connected to the lateral zones of the rear waist region always at the proper positions thereof.

With article in which, in addition to the first engageable means and the first receiving means to be anchored, there are formed in the third stretchable zones with the second engageable means and the second receiving means, the second engageable means are engaged with the second receiving means and thereby the third stretchable zones lying in the front and rear end zones are substantially connected together. In this way, the wearer's waist region can be tightened by the third stretchable zones in the circumferential direction of the wearer's waist region.

With the article, the first engageable means may be engaged with the first receiving means to place the second engageable means upon the outer side of the second receiving means. In this way, the second engageable means can be reliably engaged with the second receiving means.

DETAILED DESCRIPTION OF THE PREFERRED EMBODIMENTS

Details of an open-type disposable wearing article according to the present invention will be more fully understood from the description given hereunder with reference to the accompanying drawings.

Figure 1:
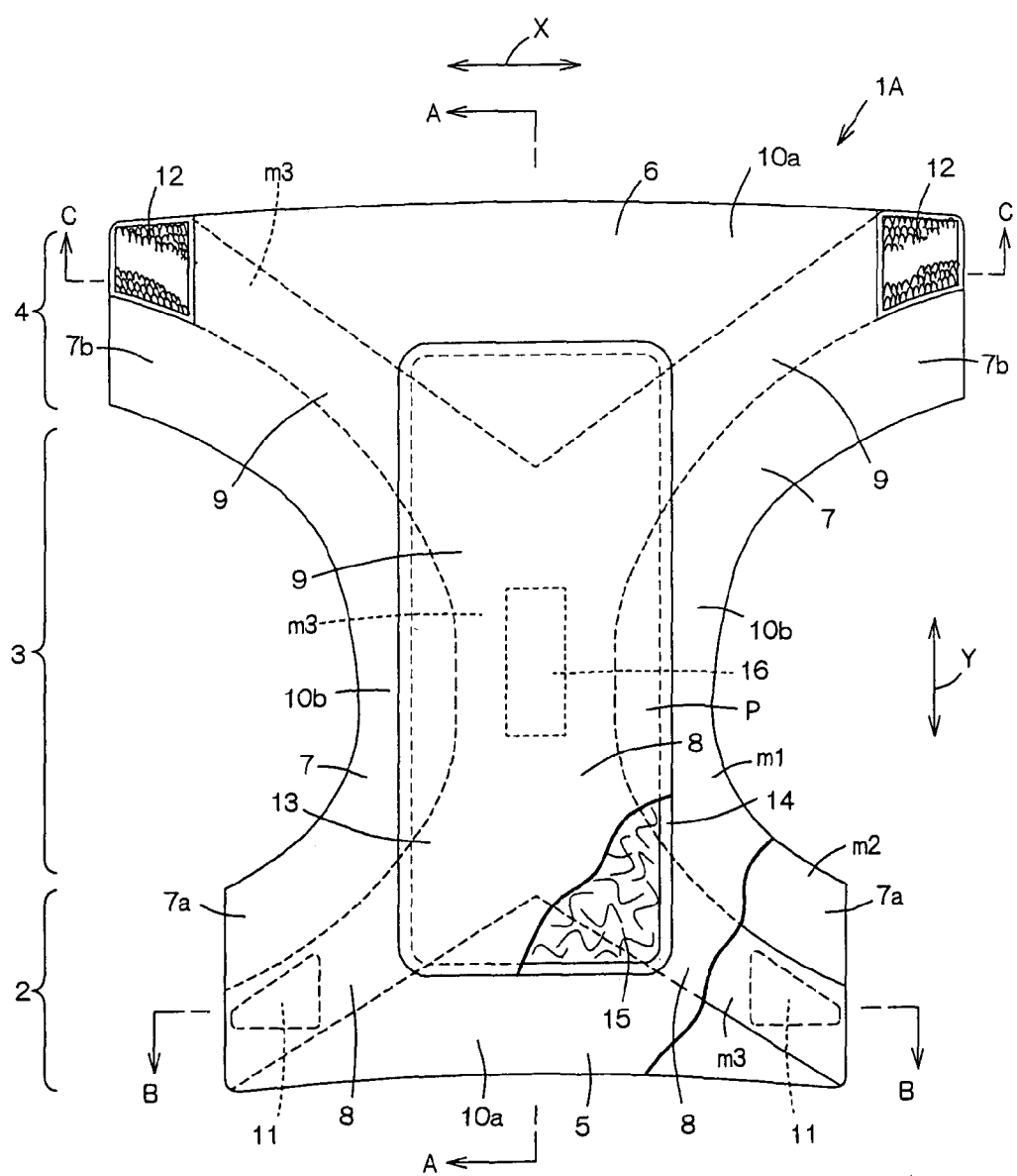
FIG. 1 is a partially cutaway plan view showing an example of the disposable wearing article.
Figure 2:
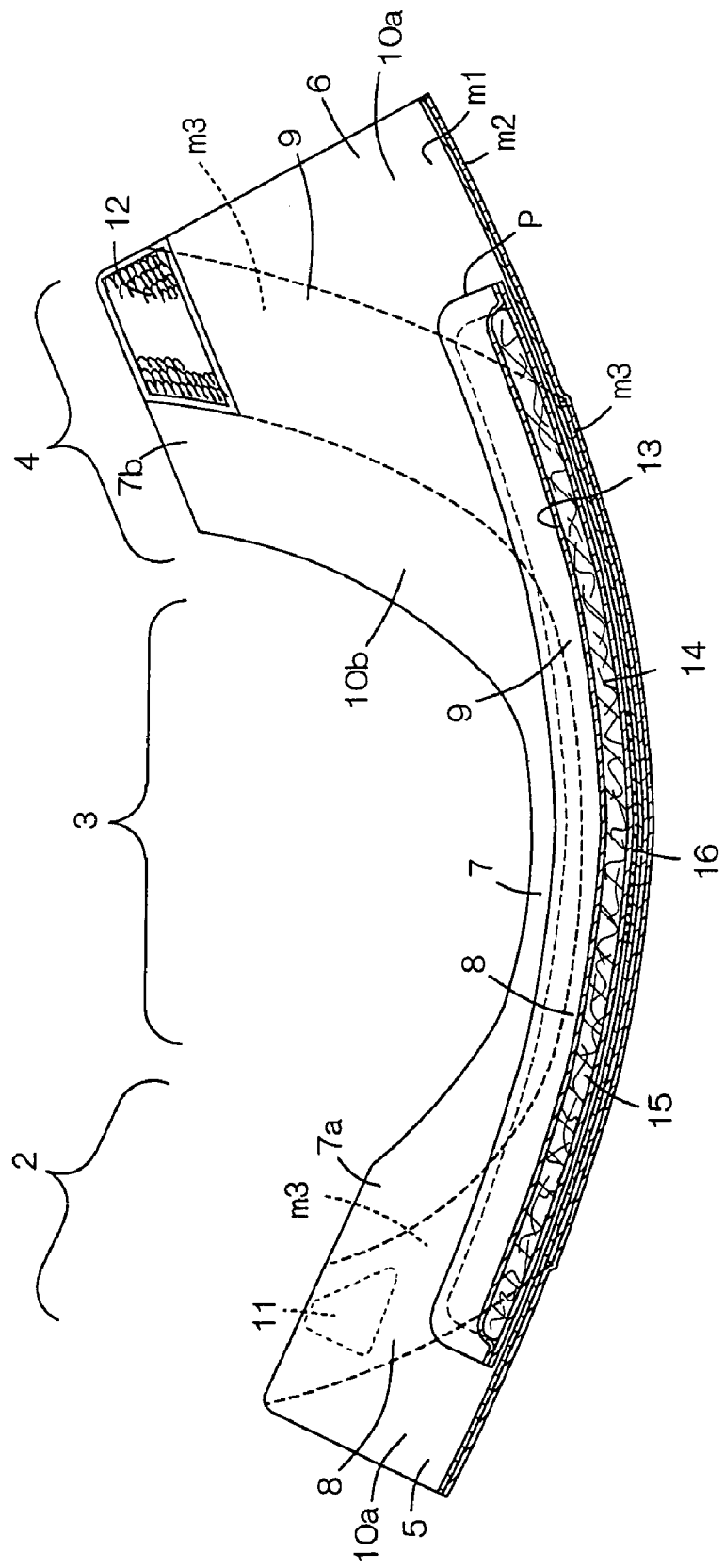
FIG. 2 is a sectional view taken along a line A—A in FIG. 1.
Figure 3:
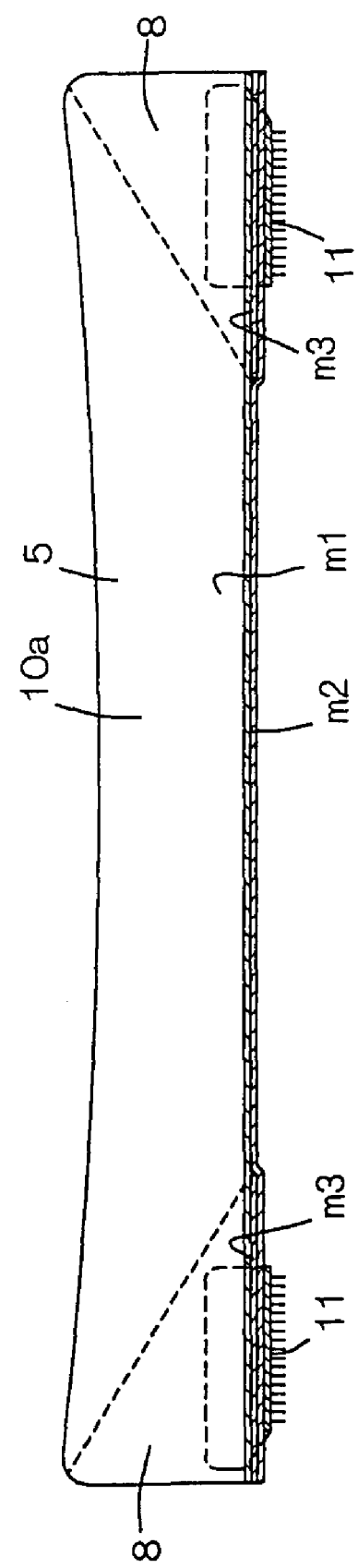
FIG. 3 is a sectional view taken along a line B—B in FIG. 1.
Figure 4:
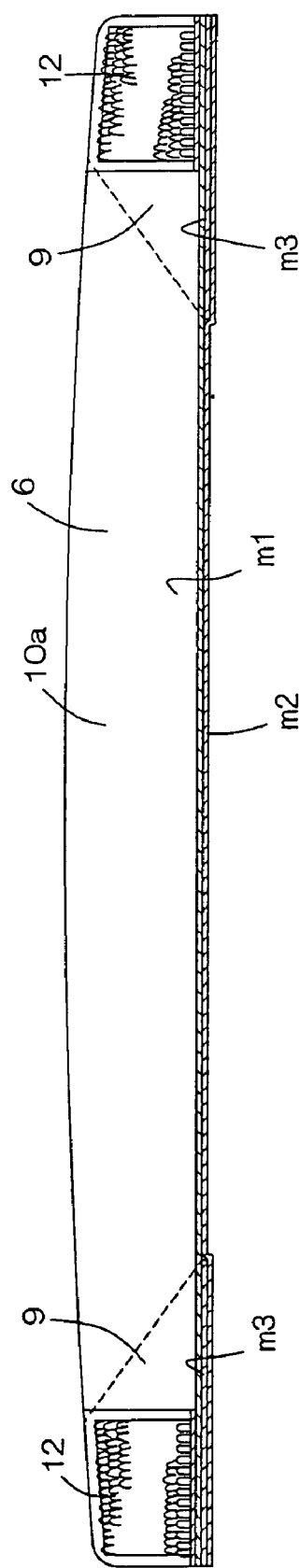
FIG. 4 is a sectional view taken along a line C—C in FIG. 1.

FIG. 1 is a partially cutaway plan view showing an example of the disposable wearing article, FIG. 2 is a sectional view taken along a line A—A in FIG. 1, FIG. 3 is a sectional view taken along a line B—B in FIG. 1 and FIG. 4 is a sectional view taken along a line C—C in FIG. 1. In FIG. 1, a transverse direction is indicated by an arrow X and a longitudinal direction is indicated by an arrow Y. Expression "inner surfaces" of fibrous nonwoven fabric layers m1, m2 as well as of top- and backsheets" refers to the surfaces thereof facing wearer's body and expression "outer surfaces" thereof refers to the surfaces thereof facing away from the wearer's body.

An article 1A is composed, as viewed in its longitudinal direction, of a front waist region 2, a rear waist region 4 and a crotch region 3 extending between these two waist regions 2, 4 and has front and rear end zones 5, 6 extending in the transverse direction and lateral zones 7 extending in the longitudinal direction. In the crotch region 3, the lateral zones 7 curve inward transversely of the article 1A so as to describe circular arcs. The article 1A is substantially hourglass-shaped as viewed in its developed state. The article 1A is provided on its surface facing the wearer's body with an absorbent pad P releasably attached thereto and this pad P serves to absorb and to contain bodily discharges.

The article 1A comprises stretchable fibrous nonwoven fabric layers m1, m2 placed upon each other. These nonwoven fabric layers m1, m2 are elastically stretchable in the transverse direction as well as in the longitudinal direction not only in the front and rear waist regions 2, 4 but also in the crotch region 3. In the article 1A, the nonwoven fabric layer m1 lies on the side of the wearer's body and the nonwoven fabric layer m2 lies on the side far from the wearer's body. In the article 1A, the surfaces of these nonwoven fabric layers m1, m2 opposed to each other are joined together intermittently so that the elastic property intrinsic to these nonwoven fabric layers m1, m2 might not be deteriorated due to joining. Specifically, these nonwoven fabric layers m1, m2 may be intermittently joined to each other in dot pattern, spiral pattern, zigzag pattern or stripe pattern. The article 1A has a first stretchable zone 8, a second stretchable zone 9 and third stretchable zones 10a, 10b defined by zones other than the first and second stretchable zones 8, 9.

The first stretchable zone 8 is bifurcated in a transverse middle 3a of the crotch region 3 so as to extend from the transverse middle 3a to lateral zones 7a in the vicinity of the front end zone 5. The second stretchable zone 9 also is bifurcated in the transverse middle 3a of the crotch region 3 so as to extend from the transverse middle 3a to lateral zones 7b in the vicinity of the rear end zone 6. In the transverse middle 3a of the crotch region 3, the first stretchable zone 8 and the second stretchable zone 9 are contiguous to each other and extend in the longitudinal direction. These first and second stretchable zones 8, 9 extend around the crotch region 3 substantially in X-shape.

The third stretchable zones 10a lie outside the first and second stretchable zones 8, 9 as viewed in the longitudinal direction and define the front and rear end zones 5, 6 of the article 1A. The third stretchable zones 10b lie outside of the first and second stretchable zones 8, 9 as viewed in the transverse direction and define the lateral zones 7 of the article 1A.

In the first and second stretchable zones 8, 9, a stretchable fibrous nonwoven fabric layer m3 is interposed between the nonwoven fabric layers m1, m2. The nonwoven fabric layer m3 also is elastically stretchable in the transverse direction as well as in the longitudinal direction and intermittently joined to the surfaces of the nonwoven fabric layers m1, m2 opposed to each other. These nonwoven fabric layers m1, m2, m3 are intermittently joined one to another under no tension. Thus the first and second stretchable zones 8, 9 respectively comprise those three fibrous nonwoven fabric layers m1, m2, m3 placed one upon another. The third stretchable zones 10a, 10b, on the other hand, respectively comprise those two fibrous nonwoven fabric layers m1, m2. Consequently, the basis weight of the nonwoven fabric layer is higher in the first and second stretchable zones 8, 9 than in the third stretchable zones 10a, 10b and the stretch stress is higher in the stretchable zones 8, 9 than in the third stretchable zones 10a, 10b.

The lateral zones 7a in the front waist region 2 are provided with first hook members 11 attached thereto. The hook members 11 are secured to an outer surface of the nonwoven fabric layer m2 in the first stretchable zone 8. Similarly, the lateral zones 7b in the rear waist region 4 are provided with first loop members 12 attached thereto. The loop members 12 are secured to an inner surface of the nonwoven fabric layer m1 in the second stretchable zone 9.

The pad P comprises a liquid-pervious topsheet 13 facing the wearer's body, a liquid-impervious backsheet 14 facing away from the wearer's body and a liquid-absorbent core 15 interposed between the top- and backsheets 13, 14 and secured to the surfaces of these top- and backsheets 13, 14 opposed to each other. The pad P constructed in this manner is attached to the inner surface of the nonwoven fabric layer m1 in the crotch region 3 of the article 1A by means of an adhesive 16 applied to the outer surface of the backsheet 14. The top- and backsheets 13, 14 are overlaid and secured to each other along marginal zones extending outward beyond a peripheral edge of the core 15.

Figure 5:
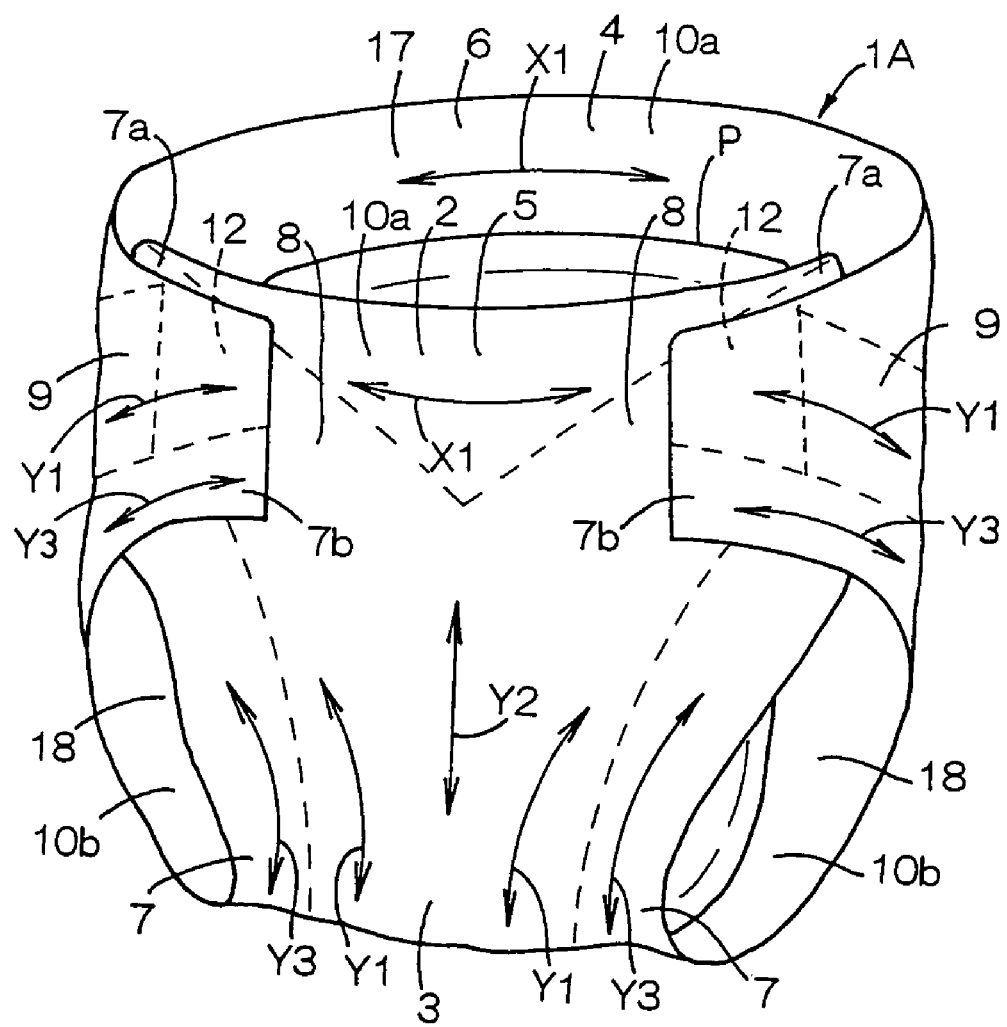
FIG. 5 is a perspective view showing the article of FIG. 1 as put on a wearer's body.
Figure 6:
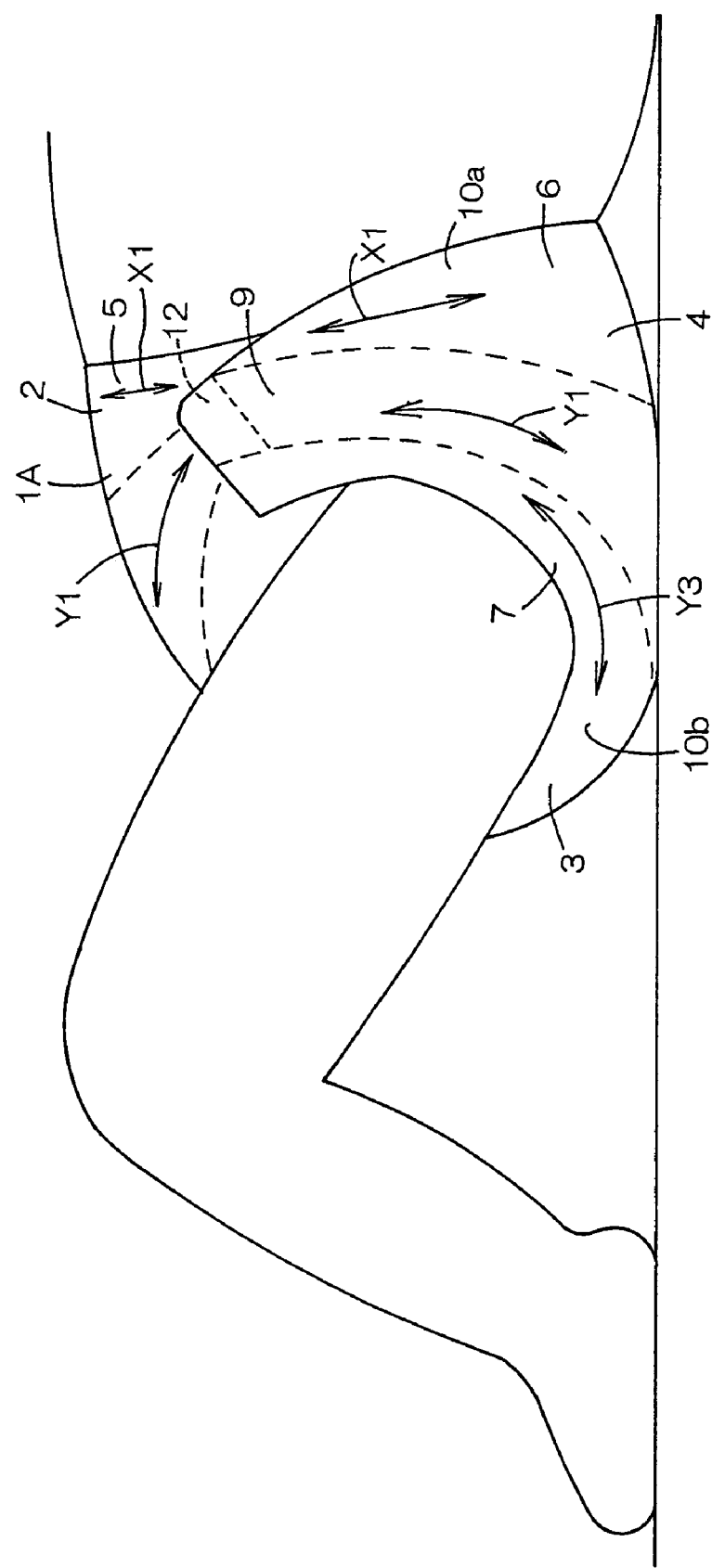
FIG. 6 is a perspective view showing the article of FIG. 1 as put on a wearer's body.

FIGS. 5 and 6 are perspective views showing the article 1A as put on the wearer's body. In FIG. 6, the wearer is illustrated as lying face up.

To wear the article 1A, the lateral zones 7b in the rear waist region 4 may be moved toward the lateral zones 7a in the front waist region 2, then placed upon the outer side of the respective lateral zones 7a and thereafter the loop members 12 may be engaged with the respective hook members 11 so as to connect the front and rear waist regions 2, 4 to each other. Upon connection of the front and rear waist regions 2, 4 in this manner, the article 1A defines a waist-hole 17 and a pair of leg-holes 18.

The first stretchable zone 8 lying in the lateral zones 7a of the front waist region 2 and the second stretchable zone 9 lying in the lateral zones 7b of the rear waist region 4 are substantially connected to each other so as to form an annular configuration as the loop members 12 come in engagement with the hook members 11. The first and second stretchable zones 8, 9 cooperate to form the annular configuration extending from a wearer's inguinal region toward a wearer's waist region as the article 1A is put on the wearer's body. In this way, the contractile force of these stretchable zones 8, 9 is effective to tighten the wearer's inguinal and waist regions in a thigh-surrounding direction indicated by an arrow Y1.

The first and second stretchable zones 8, 9 are contractible also in the longitudinal, i.e., a vertical direction indicated by an arrow Y2 so that the contractile force of these elastic zones 8, 9 in the longitudinal direction functions to pull the crotch region 3 of the article 1A upward. With consequence, it is possible for the article 1A to keep the crotch region 3 in close contact with a wearer's crotch region and therefore to keep the pad P attached to the crotch region 3 also in close contact with the wearer's crotch region.

The lateral zones 7 of the article 1A are defined by the third stretchable zones 10b having a stretch stress lower than in the first and second stretchable zones 8, 9. Wearer's thighs are surrounded with the third stretchable zones 10b in the thigh-surrounding direction indicated by an arrow Y3. Thus these third stretchable zones 10b serve, during use of the article 1A, to prevent the anxiety that the first and second stretchable zones 8, 9 might restrict free movement of the wearer's legs. The front and rear end zones 5, 6 of the article 1A defined by the third stretchable zones 10a tighten the wearer's waist region in a waist-surrounding direction indicated by the arrow X1 and thereby prevent the article 1A from unintentionally slipping down along the wearer's waist region.

The loop members 12 must be engaged with the hook members 11 to put the article 1A on the wearer's body and such engagement between these members 11, 12 necessarily results in connection between the first stretchable zone 8 and the second stretchable zone 9. In other words, it is impossible to bring the loop members 12 attached to the lateral zones 7b in the rear waist region 4 in engagement with any members or zones other than the hook members 11, for example, with the nonwoven fabric layer m1 in the front waist region 2 when it is intentioned to put the article 1A on the wearer's body. It is thus ensured that the lateral zones 7a of the front waist region 2 are connected to the lateral zones 7b of the rear waist region 4 always at the proper positions thereof.

The positions at which the hook members 11 and the loop members 12 are attached to the lateral zones 7a of the front waist region 2 and to the lateral zones 7b of the rear waist region 4, respectively, may be selectively changed as long as the hook members 11 are provided to the first stretchable zone 8 and the loop members 12 are provided to the second stretchable zone 9. The positions at which the lateral zones 7a of the front waist region 2 and the lateral zones 7b of the rear waist region 4 are connected to each other are adjusted accordingly.

The first and second stretchable zones 8, 9 exhibit a stretch stress in a range of 0.25–30N when a width of the zones 8, 9 is 15 mm and the zones 8, 9 are stretched by 15% and a stretch stress in a range of 0.6–50N when a width of the zones 8, 9 is 15 mm and the zones 8, 9 are stretched by 40%. The third stretchable zones 10a, 10b exhibit a stretch stress in a range of 0.17–20N when a width of the zones 10a, 10b is 15 mm and the zones 10a, 10b are stretched by 15% and a stretch stress in a range of 0.4–33N when a width of the zones 10a, 10b is 15 mm and the zones 10a, 10b are stretched by 40%.

If the first and second stretchable zones 8, 9 exhibit a stretch stress less than 0.25N when stretched by 15% or less than 0.6N when stretched by 40%, the contractile force of the first and second stretchable zones 8, 9 will be insufficient not only to bring the crotch region 3 of the article 1A in close contact with the wearer's crotch but also to ensure that the first and second stretchable zones 8, 9 properly tighten the inguinal region and the waist of the wearer. If the first and second stretchable zones 8, 9 exhibit a stretch stress exceeding 30N when stretched by 15% or exceeding 50N when stretched by 40%, the contractile force of the first and second stretchable zones 8, 9 in the longitudinal direction will intend to slip the article 1A down along the wearer's waist and raise an apprehension that the article 1A might be unintentionally slip down off from the proper position. In addition, the first and second stretchable zones 8, 9 will excessively tighten the wearer's inguinal region and waist and the wearer will create a feeling of discomfort against the wearer during use of the article 1A.

If the third stretchable zones 10a, 10b exhibit a stretch stress less than 0.17N when stretched by 15% or a stretch stress less than 0.4N when stretched by 40%, the contractile force of the third stretchable zones 10a in the transverse direction will be excessively low in compared to the contractile force of the first and second stretchable zones 8, 9 in the longitudinal direction. As a result, the article 1A may sometimes unintentionally slip down off from its proper position during use thereof. If the third stretchable zones 10a, 10b exhibit a stretch stress exceeding 20N when stretched by 15% or a stretch stress exceeding 33N when stretched by 40%, the contractile force of the first and second stretchable zones 8, 9 in the longitudinal direction will be restrained by the contractile force of the third stretchable zones 10a in the transverse direction depending on the stretch stress of the first and second stretchable zones 8, 9. Consequently, the expected function of these stretchable zones 8, 9 to keep the crotch region 3 of the article 1A in close contact with the wearer's crotch may be deteriorated.

It is possible to attach loop members to the first stretchable zone 8 in the lateral zones 7a of the front waist region 2 and to attach hook members to the second stretchable zone 9 in the lateral zones 7b of the rear waist region 4. It is also possible to coat the second stretchable zone 9 in the lateral zones 7b of the rear waist region 4 with self-adhesives and to provide on the first stretchable zone 8 in the lateral zones 7a of the front waist region 2 with films attached thereto so as to be releasably attached to the adhesives.

Figure 7:
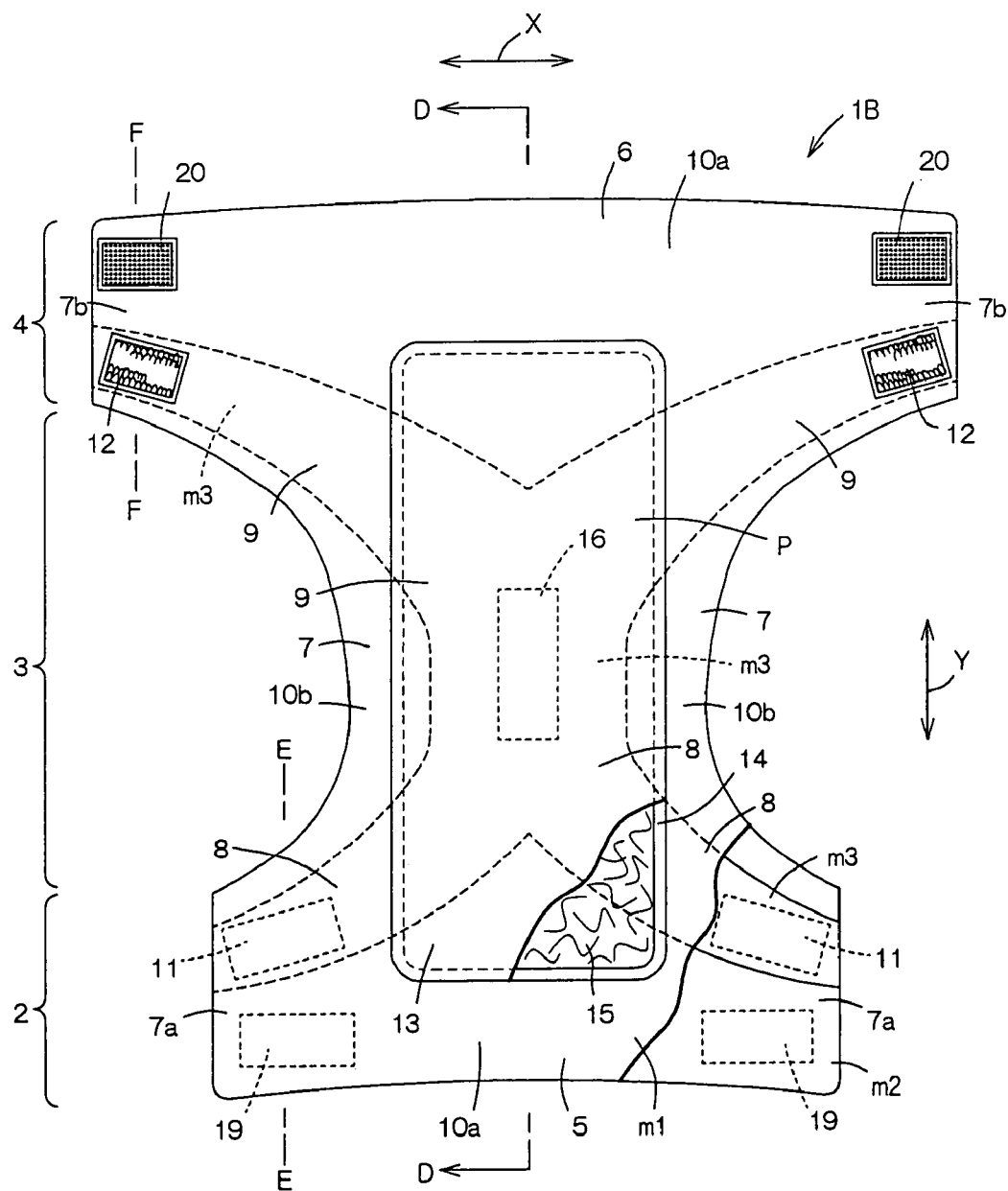
FIG. 7 is a partially cutaway plan view showing another example of the disposable wearing article.
Figure 8:
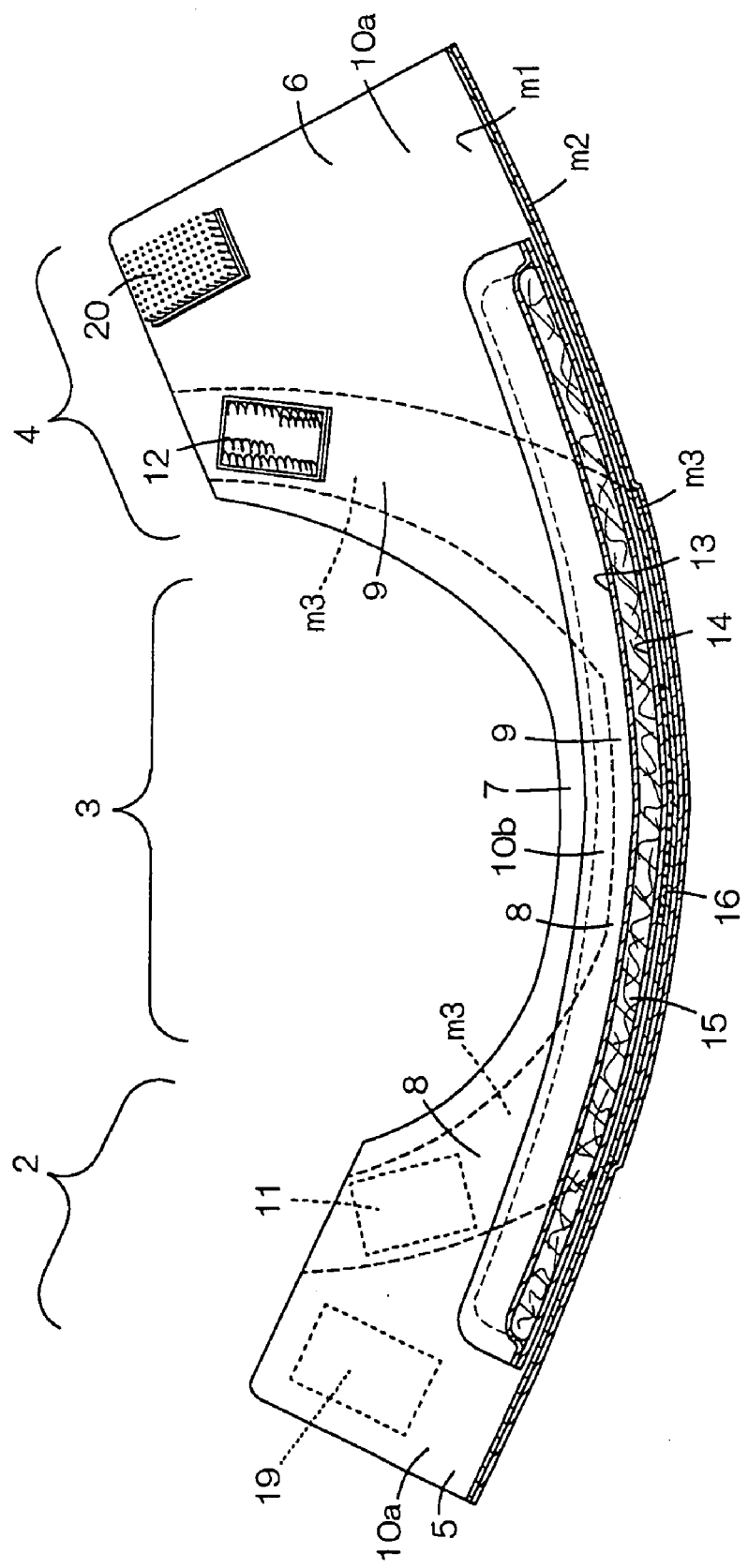
FIG. 8 is a sectional view taken along a line D—D in FIG. 7.
Figure 9:
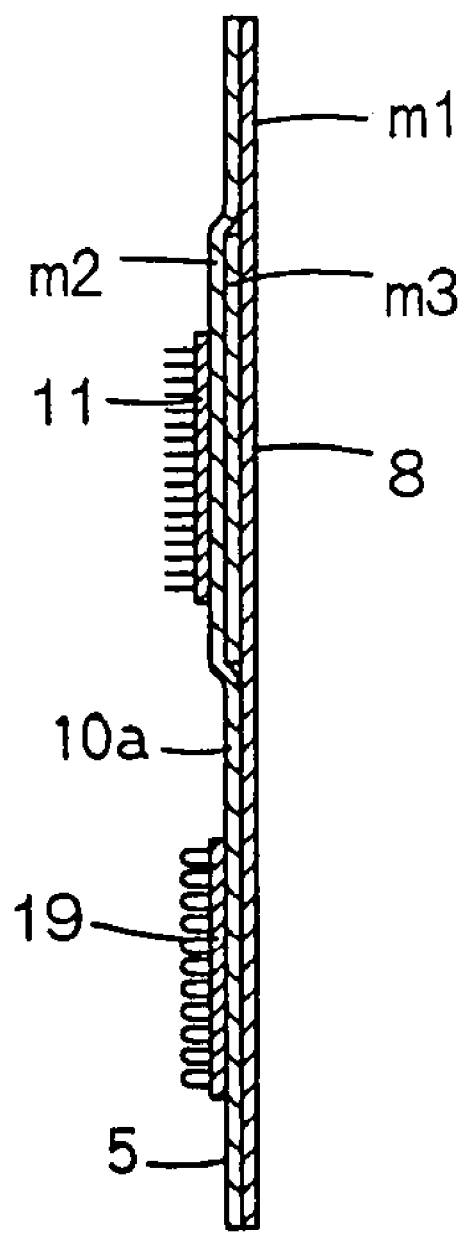
FIG. 9 is a sectional view taken along a line E—E in FIG. 7.
Figure 10:
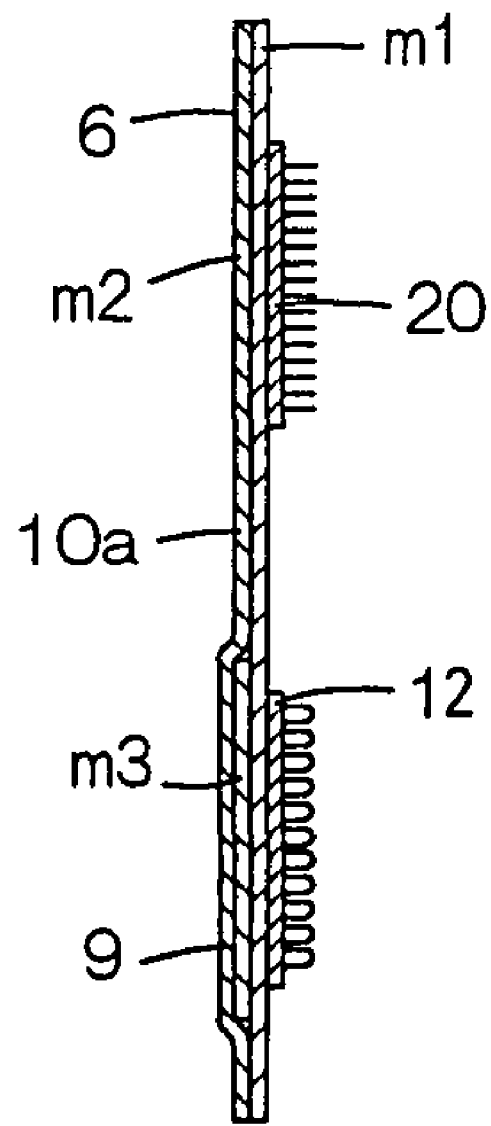
FIG. 10 is a sectional view taken along a line F—F in FIG. 7.

FIG. 7 is a partially cutaway plan view showing another example 1B of the disposable wearing article, FIG. 8 is a sectional view taken along a line D—D in FIG. 7, FIG. 9 is a sectional view taken along a line E—E in FIG. 7 and FIG. 10 is a sectional view taken along a line F—F in FIG. 7. In FIG. 7, a transverse direction is indicated by an arrow X and a longitudinal direction is indicated by an arrow Y.

An article 1B is composed of a front waist region 2, a rear waist region 4 and a crotch region 3 extending between these two waist regions 2, 4 and has front and rear end zones 5, 6 extending in the transverse direction and lateral zones 7 extending in the longitudinal direction. In the crotch region 3, the lateral zones 7 curve inward transversely of the article 1B so as to describe circular arcs. The article 1B is provided on its surface facing the wearer's body with an absorbent pad P releasably attached thereto and this pad P comprises an absorbent core 15 interposed between a liquid-pervious topsheet 13 and a liquid-impervious backsheet 14.

The article 1B comprises elastically stretchable fibrous nonwoven fabric layers m1, m2 placed upon each other. These nonwoven fabric layers m1, m2 are elastically stretchable in the transverse direction as well as in the longitudinal direction not only in the front and rear waist regions 2, 4 but also in the crotch region 3. The article 1B is thus elastically stretchable in the transverse direction as well as in the longitudinal direction in all regions, i.e., in the front and rear waist regions 2, 4 and in the crotch region 3. In the article 1B, the surfaces of these nonwoven fabric layers m1, m2 opposed to each other are joined together intermittently. The article 1B has a first stretchable zone 8, a second stretchable zone 9 and third stretchable zones 10a, 10b defined by the remaining regions with respect to those first and second stretchable zones 8, 9.

The first stretchable zone 8 is bifurcated in a transverse middle 3a of the crotch region 3 so as to extend from the transverse middle 3a to lateral zones 7a in the vicinity of the front end zone 5. The second stretchable zone 9 also is bifurcated in the transverse middle 3a of the crotch region 3 so as to extend from the transverse middle 3a to lateral zones 7b in the vicinity of the crotch region 3. In the transverse middle 3a of the crotch region 3, the first stretchable zone 8 and the second stretchable zone 9 are contiguous to each other and extend in the longitudinal direction. These first and second stretchable zones 8, 9 extend around the crotch region 3 substantially in X-shape.

The third stretchable zones 10a lie outside the first and second stretchable zones 8, 9 as viewed in the longitudinal direction and define the front and rear end zones 5, 6 of the article 1B. The third stretchable zones 10b lie outside of the first and second stretchable zones 8, 9 as viewed in the transverse direction and define the lateral zones 7 of the article 1A.

In the first and second stretchable zones 8, 9, a stretchable fibrous nonwoven fabric layer m3 is interposed between the nonwoven fabric layers m1, m2. The nonwoven fabric layer m3 also is elastically stretchable in the transverse direction as well as in the longitudinal direction and intermittently joined to the surfaces of the nonwoven fabric layers m1, m2 opposed to each other. These nonwoven fabric layers m1, m2, m3 are intermittently joined one to another under no tension. Thus the first and second stretchable zones 8, 9 respectively comprise those three fibrous nonwoven fabric layers m1, m2, m3 placed one upon another. The third stretchable zones 10a, 10b, on the other hand, respectively comprise those two fibrous nonwoven fabric layers m1, m2. Consequently, the basis weight of the nonwoven fabric layer is higher in the first and second stretchable zones 8, 9 than in the third stretchable zones 10a, 10b and the stretch stress is higher in the stretchable zones 8, 9 than in the third stretchable zones 10a, 10b.

The lateral zones 7a in the front waist region 2 are provided with first hook members 11 and second loop members 19. The hook members 11 are secured to an outer surface of the nonwoven fabric layer m2 in the first stretchable zone 8. The loop members 19 lie in the third stretchable zones 10a placed aside from the first stretchable zone 8 toward the front end zone 5 and secured to the outer surface of the nonwoven fabric layer m2.

The lateral zones 7b in the rear waist region 4 are provided with first loop members 12 and second hook members 20. The loop members 12 are secured to an inner surface of the nonwoven fabric layer m1 in the second stretchable zone 9. The hook members 20 lie in the third stretchable zones 10a placed aside from the second stretchable zone 9 toward the rear end zone 6 and secured to the inner surface of the nonwoven fabric layer m1.

Figure 11:
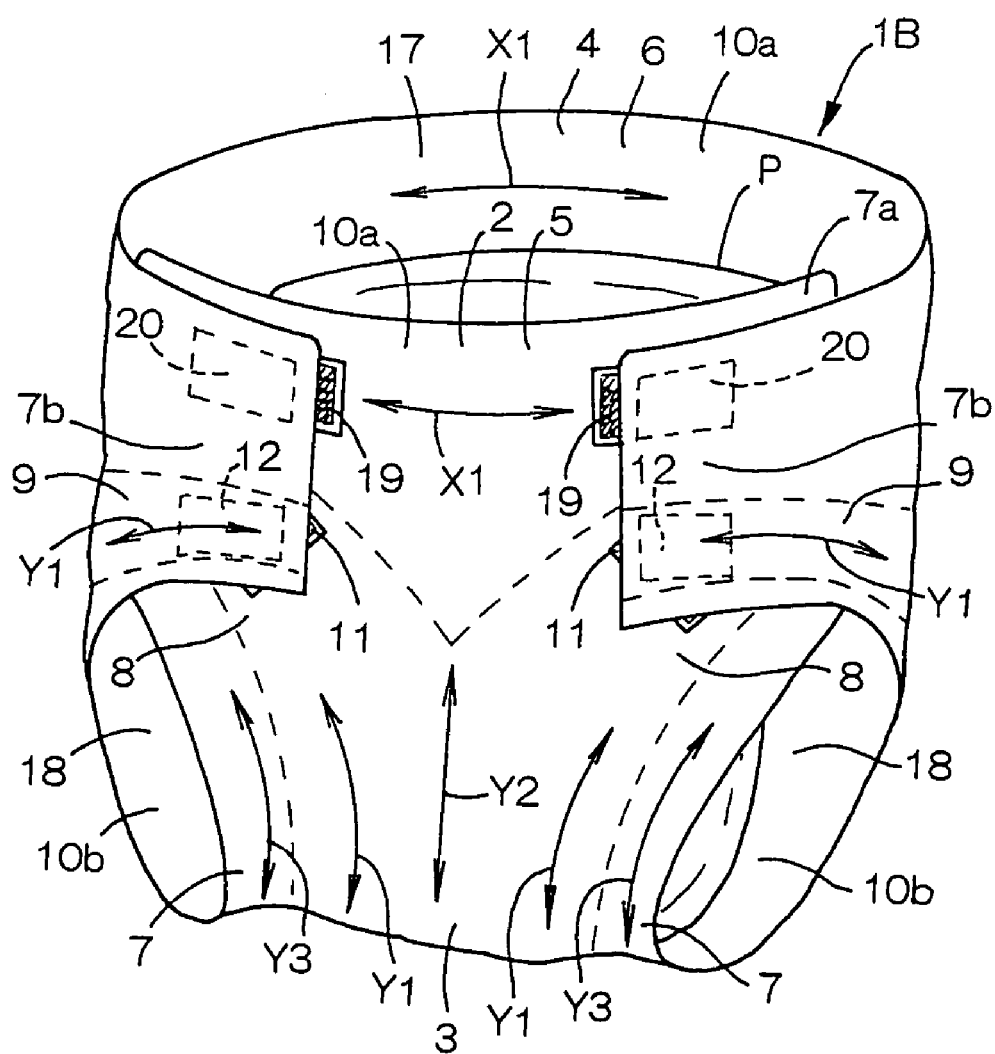
FIG. 11 is a perspective view showing the article of FIG. 7 as put on a wearer's body.

FIG. 11 is a perspective views showing the article 1B. To wear the article 1B, the lateral zones 7b in the rear waist region 4 may be moved toward the lateral zones 7a in the front waist region 2, then placed upon the outer side of the respective lateral zones 7a and thereafter the loop members 12 may be engaged with the respective hook members 11 so as to connect the front and rear waist regions 2, 4 to each other.

Upon engagement of the loop members 12 with the respective hook members 11, the first stretchable zone 8 lying in the lateral zones 7a of the front waist region 2 and the second stretchable zone 9 lying in the lateral zones 7b of the rear waist region 4 are substantially connected to each other so as to form an annular configuration. The first and second stretchable zones 8, 9 cooperate to form an annular configuration extending from the wearer's inguinal region toward the wearer's waist region as the article 1B is put on the wearer's body. In this way, the contractile force of these stretchable zones 8, 9 is effective to tighten the wearer's inguinal and waist regions in the thigh-surrounding direction indicated by an arrow Y1.

The first and second stretchable zones 8, 9 are contractible in the longitudinal, i.e., the vertical direction indicated by an arrow Y2 so that the contractile force of these elastic zones 8, 9 in the longitudinal direction functions to pull the crotch region 3 of the article 1B upward. With consequence, it is possible for the article 1B to keep the crotch region 3 in close contact with a wearer's crotch region and therefore to keep the pad P attached to the crotch region 3 also in close contact with the wearer's crotch region.

The lateral zones 7 of the article 1B are defined by the third stretchable zones 10b having a stretch stress lower than in the first and second stretchable zones 8, 9. Wearer's thighs are surrounded with the third stretchable zones 10b in the thigh-surrounding direction indicated by an arrow Y3.

The first loop members 12 must be engaged with the first hook members 11 to put the article 1B on the wearer's body and such engagement between these members 11, 12 necessarily results in connection between the first stretchable zone 8 and the second stretchable zone 9. In other words, it is impossible to bring the first loop members 12 attached to the lateral zones 7b in the rear waist region 4 in engagement with any members or zones other than the first hook members 11, for example, with the nonwoven fabric layer m1 in the front waist region 2 when it is intentioned to put the article 1B on the wearer's body. It is thus ensured that the lateral zones 7a of the front waist region 2 are connected to the lateral zones 7b of the rear waist region 4 always at the proper positions thereof. The positions at which the hook members 1 and the loop members 12 are attached to the lateral zones 7a of the front waist region 2 and to the lateral zones 7b of the rear waist region 4, respectively, may be selectively changed. The positions at which the lateral zones 7a of the front waist region 2 are connected with the lateral zones 7b of the rear waist region 4 are adjusted accordingly.

The second hook members 20 are placed upon the outer surfaces of the second loop members 19 as the first loop members 12 are engaged with the first hook members 11, so the second hook members 20 can be reliably engaged with the second loop members 19. In the article 1B, the third stretchable zones 10a lying in the front and rear end zones 5, 6 can be substantially connected to each other as the second hook members 20 are engaged with the second loop members 29. In this way, the front and rear end zones 5, 6 defined by these third stretchable zones 10a tighten the wearer's waist region in the waist-surrounding direction indicated by an arrow X1 and thereby prevent the article 1B from unintentionally slipping down along the wearer's waist.

A stretch stress exhibited by the first and second stretchable zones 8, 9 when a width of the zones 8, 9 is 15 mm and the zones 8, 9 are stretched by 15% and when a width of the zones 8, 9 is 15 mm and the zones 8, 9 are stretched by 40% are same as those in the case of FIG. 1. A stretch stress exhibited by the third stretched zones 10a, 10b when a width of the zones 10a, 10b is 15 mm and the zones 10a, 10b are stretched by 15% and when a width of the zone is 10a, 10b is 15 mm and the zones 10a, 10b are stretched by 40% are also same as those in the case of FIG. 1.

It is possible to attach the loop members 12 to the first stretchable zone 8 in the lateral zones 7a of the front waist region 2 and to attach the hook members 11 to the second stretchable zone 9 in the lateral zones 7b of the rear waist region 4. It is also possible to attach the hook members 20 to the third stretchable zones 10a placed aside from the first stretchable zone 8 toward the front end zone 5 and to attach the loop members 19 to the third stretchable zones 10a placed aside from the second stretchable zone 9 toward the rear end zone 6.

It is possible to attach one of a hook member and a loop member to the first stretchable zone 8 in the lateral zones 7a of the front waist region 2 and the third stretchable zones 10a placed aside from the first stretchable zone 8 toward the front end zone 5 and to attach the other one of the hook member and the loop member to the second stretchable zone 9 in the lateral zones 7b of the rear waist region 4 and the third stretchable zones 10a placed aside from the second stretchable zone 9 toward the rear end zone 6, or vice versa.

It is also possible to coat the second stretchable zone 9 in the lateral zones 7b of the rear waist region 4 and the third stretchable zones 10a placed aside from the second stretchable zone 9 toward the rear end zone 6 with an adhesive and to provide on the first stretchable zone 8 in the lateral zones 7a of the front waist region 2 and on the third stretchable zones 10a placed aside from the first stretchable zone 8 toward the front end zone 5 with a film attached thereto so as to be releasably attached to the adhesive.

As a stock material for the elastically stretchable fibrous nonwoven fabric layers m1, m2, m3, melt blown or spun bond fibrous nonwoven fabric may be used. As component fibers constituting these nonwoven fabric layers m1, m2, m3, stretchable fibers obtained by melt spinning thermoplastic elastomer resin may be used.

It is possible to use, as a stock material for the nonwoven fabric layers m1, m2, m3, a composite nonwoven fabric comprising an elastically stretchable hydrophobic fibrous nonwoven fabric made of thermoplastic elastomer resin fibers and a hydrophobic fibrous nonwoven fabric made of crimped fibers, obtained by melt spinning thermoplastic synthetic resin selected from the group consisting of polypropylene, polyethylene and polyester which is placed upon at least one surface of the elastically stretchable hydrophobic fibrous nonwoven fabric. In the article 1A, 1B, the nonwoven fabric layers m1, m2, m3 may be replaced by an elastically stretchable liquid-impervious plastic film.

A stock material for the topsheet 13 may be selected from the group including a hydrophilic fibrous nonwoven fabric, a hydrophobic fibrous nonwoven fabric having a plurality of pores and liquid-pervious plastic film having a plurality of fine pores. A stock material for the backsheet 14 may be selected from the group consisting a hydrophobic fibrous nonwoven fabric, a breathable liquid-impervious plastic film, a composite nonwoven fabric comprising two hydrophobic fibrous nonwoven fabric layers laminated one upon another and a composite sheet comprising a hydrophobic fibrous nonwoven fabric and a breathable liquid-impervious plastic film laminated one upon another.

The nonwoven fabric used as a stock material for the top- and backsheet 13, 14 may be selected from the group consisting of products obtained by spun lace-, needle punch-, melt blown-, thermal bond-, spun bond-, chemical bond- and air through-processes. Component fibers constituting the nonwoven fabric may be selected from the group consisting of polyolefin-, polyester- and polyamide-based fibers and core-sheath or side-by-side type conjugated fibers of polyethylene/polypropylene or polyethylene/polyester.

The core 15 comprises a mixture of fluff pulp and super-absorbent polymer particles or a mixture of fluff pulp, super-absorbent polymer particles and thermoplastic synthetic resin fibers, in both cases, compressed to a given thickness. Preferably, the core 15 is entirely wrapped with a liquid-pervious sheet such as a tissue paper or a hydrophilic fibrous nonwoven fabric in order to prevent the core 15 from getting out of its proper shape and/or to avoid falling off of the polymer particles from the core 15. The polymer particles may be selected from the group consisting of a starch-, cellulose- and synthetic polymer-based particles.

Joining of the nonwoven fabric layers m1, m2, m3 one to another, joining of the top- and backsheets 13, 14 to each other and securing of the core 15 to the top- and backsheets 13, 14 may be achieved by use of welding means such as a heat sealing or a sonic sealing.

The article 1A, 1B as has been described with reference to the accompanying drawings is suitable as a diaper cover adapted to be used together with the absorbent pad P attached to the inner surface thereof.

What is claimed is:

1. An open-type disposable wearing article comprising:
   an elastically stretchable front waist region;
   an elastically stretchable rear waist region;
   an elastically stretchable crotch region extending between said front waist region and said rear waist region and, said front and rear waist regions being connectable with each other in opposite lateral zones thereof;
   a first stretchable zone bifurcated at a transverse middle of said crotch region so as to extend in two laterally separated portions to said opposite lateral zones of said front waist region, said first stretchable zone having a substantially uniform tensile stress;
   a second stretchable zone bifurcated at said transverse middle of said crotch region so as to extend in two laterally separated portions to said opposite lateral zones of said rear waist region, said second stretchable zone having a substantially uniform tensile stress; and
   third stretchable zones defined by zones other than said first and second stretchable zones, including extending between the two laterally separated portions of each of the first stretchable zone and the second stretchable zone and along lateral side portions of at least the crotch region, a tensile stress of said first and second stretchable zones being higher than a tensile stress of said third stretchable zones;
   first engageable means for connecting said front and rear waist regions with each other, said first engageable means being provided in said second stretchable zone in said opposite lateral zones of said rear waist region;
   first receiving means releasably engageable with said first engageable means, said first receiving means being provided in said first stretchable zone in said opposite lateral zones; and
   second engageable means for connecting said front and rear waist regions to one another are provided in said third stretchable zones lying in said opposite lateral zones of said rear waist region and second receiving means for releasably engaging said second engageable means are provided in said third stretchable zones lying in said opposite lateral zones of said front waist region.

2. The wearing article according to claim 1, wherein said first stretchable zone and said second stretchable zone are contiguous to each other at said transverse middle of said crotch region.

3. The wearing article according to claim 1, wherein said first engageable means comprise first loop members attached to an inner surface of said rear waist region in said opposite lateral zones thereof and said first receiving means comprise first hook members attached to an outer surface of said front waist region in said opposite lateral zones thereof.

4. The wearing article according to claim 1, wherein said second engageable means comprise second hook members attached to said inner surface of said rear waist region in said opposite lateral zones thereof and said second receiving means comprise second loop members attached to said outer surface of said front waist region in said opposite lateral zones thereof.

5. The wearing article according to claim 1, wherein said first stretchable zone lying in said opposite lateral zones of said front waist region and said second stretchable zone lying in said opposite lateral zones of said rear waist region are substantially connected with each other as said first engageable means are engaged with said first receiving means to put said wearing article on the wearer's body.

6. The wearing article according to claim 1, wherein said wearing article further comprises an elastically stretchable fibrous nonwoven fabric having a basis weight thereof higher in said first and second stretchable zones than in said third stretchable zones.

7. The wearing article according to claim 1, wherein said first and second stretchable zones have a tensile stress in a range of 0.25–30N when a width of said zones is 15 mm and said zones are stretched by 15% and a tensile stress in a range of 0.6–50N when a width of said zones is 15 mm and said zones are stretched by 40% and wherein said third stretchable zone have a tensile stress in a range of 0.17–20N when a width of said zone is 15 mm and said zone is stretched by 15% and a tensile stress in a range of 0.4–33N when a width of said zone is 15 mm and said zone is stretched by 40%.

8. The wearing article according to claim 1, wherein said wearing article comprises a diaper cover used in combination with an absorbent pad that is attached to a surface of said wearing article that faces a wearer's body.

* * * * *

UNITED STATES PATENT AND TRADEMARK OFFICE
CERTIFICATE OF CORRECTION

PATENT NO. : 7,122,024 B2
APPLICATION NO. : 10/603008
DATED : October 17, 2006
INVENTOR(S) : Nakajima et al.

It is certified that error appears in the above-identified patent and that said Letters Patent is hereby corrected as shown below:

Title Page (73) Assignee

Insert --UNI-CHARM CORPORATION  Ehime-Ken, (JP)--

Signed and Sealed this

Twenty-seventh Day of March, 2007

JON W. DUDAS
*Director of the United States Patent and Trademark Office*